United States Patent
Lord, III et al.

(10) Patent No.: US 9,574,140 B2
(45) Date of Patent: *Feb. 21, 2017

(54) REMOVING MERCURY FROM CRUDE OIL

(71) Applicant: ConocoPhillips Company, Houston, TX (US)

(72) Inventors: Charles J Lord, III, Bartlesville, OK (US); Lars T Lambertsson, Umeå (SE); Erik L. Björn, Umeaå (SE); Wolfgang Frech, Umeå (SE); Sally A. Thomas, Bartlesville, OK (US)

(73) Assignee: ConocoPhillips Company, Houston, TX (US)

( * ) Notice: Subject to any disclaimer, the term of this patent is extended or adjusted under 35 U.S.C. 154(b) by 355 days.

This patent is subject to a terminal disclaimer.

(21) Appl. No.: 14/173,985

(22) Filed: Feb. 6, 2014

(65) Prior Publication Data
US 2015/0218462 A1 Aug. 6, 2015
US 2016/0333278 A9 Nov. 17, 2016

Related U.S. Application Data

(60) Provisional application No. 61/783,817, filed on Mar. 14, 2013.

(51) Int. Cl.
*C10G 31/06* (2006.01)
*C10G 29/00* (2006.01)
(Continued)

(52) U.S. Cl.
CPC .............. *C10G 31/06* (2013.01); *C10G 21/06* (2013.01); *C10G 21/14* (2013.01); *C10G 25/003* (2013.01);
(Continued)

(58) Field of Classification Search
CPC ......... C10G 31/06; C10G 21/06; C10G 21/14; C10G 25/003; C10G 29/00; C10G 53/02; C10G 53/04; C10G 53/08
See application file for complete search history.

(56) References Cited

U.S. PATENT DOCUMENTS

3,194,629 A 7/1965 Driebelbis
3,857,704 A 12/1974 Coulter
(Continued)

FOREIGN PATENT DOCUMENTS

WO 2012046057 7/2012
WO PCT/US2014/15011 5/2014

OTHER PUBLICATIONS

Audeh, C.A., (1993). ACS Division of Fuel Chemistry, Chicago, IL, 787-794.*
(Continued)

*Primary Examiner* — Brian McCaig
(74) *Attorney, Agent, or Firm* — Boulware & Valoir

(57) ABSTRACT

Methods, systems and designs are provided for removing mercury from crudes. Crude oil is heated to a temperature above 100° C. and held at that temperature for a specified period of time to convert all of the forms of mercury in the oil into the elemental mercury form. The elemental mercury is then stripped from the crude oil by e.g., flashing the hot oil and/or contacting it with a gas phase. This process transfers the elemental mercury from the oil phase into the gas phase. Elemental mercury can then be removed from the gas phase by methods such as condensation, precipitation, or absorption either alone or in combination.

18 Claims, 5 Drawing Sheets

Values from Literature for Concentrations of Mercury in Crude Oil
(range shown by vertical; average, or recommended value indicated by circle)

(51) Int. Cl.
- C10G 21/06 (2006.01)
- C10G 21/14 (2006.01)
- G01N 33/28 (2006.01)
- C10G 25/00 (2006.01)
- C10G 53/02 (2006.01)
- C10G 53/04 (2006.01)
- C10G 53/08 (2006.01)

(52) U.S. Cl.
 CPC .............. *C10G 29/00* (2013.01); *C10G 53/02* (2013.01); *C10G 53/04* (2013.01); *C10G 53/08* (2013.01); *G01N 33/2858* (2013.01); *C10G 2300/205* (2013.01)

(56) References Cited

U.S. PATENT DOCUMENTS

| | | | |
|---|---|---|---|
| 4,962,276 | A | 10/1990 | Yan |
| 5,384,040 | A | 1/1995 | Barthel |
| 5,510,565 | A | 4/1996 | Tan |
| 6,350,372 | B1 | 2/2002 | Degnan |
| 6,537,443 | B1 | 3/2003 | Frankiewicz |
| 6,685,824 | B2 | 2/2004 | Frankiewicz |
| 6,806,398 | B2 | 10/2004 | Sakai |
| 6,942,840 | B1 | 9/2005 | Broderick |
| 8,080,156 | B2 | 12/2011 | Cross |
| 8,221,711 | B1* | 7/2012 | Lee ........................ B01D 53/64 210/688 |
| 2012/0073601 | A1 | 3/2012 | Lord, III |
| 2013/0225897 | A1* | 8/2013 | Candelon ................ C07C 7/148 585/802 |

OTHER PUBLICATIONS

Tran, K-Q, et al. (2011). Selenium Filter and Removal of Mercury From Flue Gas, Department of Environmental Inorganic Chemistry, Chalmers University of Technology 412-96 Goteborg, Sweden, http://www.transjonic.se/Hg.htm (Printed from Internet Nov. 8, 2011).*
Wilhelm, S.M. et al. (2006). Energy & Fuels, 20, 180-186.*
Salvá, C., et al., "Mercury Removal Process is Applied to Crude Oil of Southern Argentina", SPE 138333 (2010).
Hollebone, B.P. et al., "Mercury in Crude Oil Refined in Canada", Environment Canada, Ottawa, ON, 2007.
Taube, "Soil remediation—mercury speciation in soil and vapor phase during thermal treatment", Water Air Soil Pollut., vol. 193, p. 155-163 (Apr. 2008).
DKL Engineering, Inc, Gas Cleaning System—Mercury Removal, p. 1-6 (Apr. 2008).
Nsengimana, "Speciation of Organometallic of Tin, Lead, and Mercury in Environmental Samples," U. of Witwatersrand (2007).
Search report for EP counterpart, Application No. 14762967, Issued Sep. 30, 2016.

* cited by examiner

Figure 1  Values from Literature for Concentrations of Mercury in Crude Oil
(range shown by vertical; average, or recommended value indicated by circle)

Process for Removal of Mercury from Crude Oil

REMOVING MERCURY FROM CRUDE OIL

PRIOR RELATED APPLICATIONS

This application claims priority to U.S. Ser. No. 61/783,817, filed Mar. 14, 2013, which is expressly incorporated by reference herein in its entirety.

FEDERALLY SPONSORED RESEARCH STATEMENT

Not applicable.

REFERENCE TO MICROFICHE APPENDIX

Not applicable.

FIELD OF THE DISCLOSURE

The disclosure generally relates to removing mercury from crude oils.

BACKGROUND OF THE DISCLOSURE

Coal is the largest source of human-generated mercury emissions in the United States. Coal-fired power plants release about 48 tons of mercury annually, according to EPA data. In contrast, the total amount of mercury in crude oil processed in the U.S. annually is less than five percent of the amount contained in the U.S. coal produced and consumed annually.

Mercury concentrations in crude oil have been reported from as low as <1 ng/g to as high as 50,000 ng/g of oil (see e.g., FIG. 1). Some of the variability observed in crude oil mercury data is due to difficulties encountered in performing the analyses. A wide variety of measurement techniques, including neutron activation and many types of sample preparation systems coupled with detectors as diverse as mass spectrometers, ICP/MS, atomic absorption, and atomic fluorescence have been used to perform these analyses. As such, it can be very difficult to compare mercury analysis results obtained in different laboratories using different analytical techniques. The handling of samples can also significantly affect the measured results. A recent study found that the number of times a sample bottle had been opened could significantly affect the measured concentration.

Although analytical difficulties are responsible for some of the variability in crude oil mercury data, geological factors such as depositional environment and thermal history are more important influence on the concentrations of mercury that are observed in currently produced oils. The mercury concentrations shown in FIG. 1 vary by more than a factor of 1000, which is largely indicative of the wide variety of environments from which these oils originate.

Mercury has come under increasing scrutiny in recent years because its presence in oil creates problems throughout the production, transportation, storage and refining systems. These problems include environmental concerns, contamination of refinery products, catalyst poisoning, corrosion of equipment, health risks for personnel, as well as expenses for disposal of contaminated tank sludge, cleaning of contaminated equipment, shipping restrictions, etc. These issues have led companies to search for methods of reducing the mercury content of crude oil.

Several processes for removing mercury from crude oil have been disclosed in U.S. Pat. No. 6,350,372, U.S. Pat. No. 6,537,443, U.S. Pat. No. 6,685,824, and U.S. Pat. No. 6,806,398 and in an article by Salva (2010). All of these processes essentially involve reacting the crude oil with a sulfur compound to precipitate HgS and then separating the HgS particles from the oil by filtration or another technique for solids removal. In some cases the process requires an additional filtration step prior to contacting the oil with the sulfur compound.

Such processes require the addition of reagent chemicals as well as filtration of the crude oil. The filtration step in particular is problematic because of filter plugging by other components in the crude oil such as waxes and sediments. The HgS will only comprise a small percentage of the total solids removed by filtration. The maintenance of a crude oil filtration unit can become cost prohibitive in terms of manpower, filtration media, and disposal.

The process disclosed in U.S. Pat. No. 8,080,156, in contrast, involves the use of natural gas to strip mercury from the crude oil. However, this process is only effective for the removal of elemental mercury. The efficiency of this process is thus limited by the ratio of elemental mercury to total mercury in the oil, and, in some cases, the efficiency of mercury removal can be very low.

Thus, what are needed in the art are better methods of evaluating and removing mercury from crude hydrocarbons.

SUMMARY OF THE DISCLOSURE

The disclosure utilizes our discovery that the thermal reduction of ionic mercury to elemental mercury can be carried out at moderate temperatures and within a commercially feasible timeframe in a crude oil matrix.

A new method for determining the forms of mercury and their respective concentrations in a crude oil sample is described. This will allow for the development of a reaction rate expression for that particular crude oil feed.

The use of reaction rate expressions specific to the crude oil feed in the process enables us to calculate optimum design specifications such as process temperature, vessel sizes, oil feed rate, oil recycle rate, etc.

Generally speaking, crude oil is heated to a temperature above 100° C. and held at that temperature for a specified period of time to convert all of the forms of mercury in the oil into the elemental mercury form. The rate of conversion to elemental mercury increases with temperature, and also varies with the profile of components in the crude.

The elemental mercury is then stripped from the crude oil by e.g., flashing the hot oil and/or contacting it with a gas phase. This process transfers the elemental mercury from the oil phase into the gas phase. Elemental mercury can then be removed from the gas phase by methods such as condensation, precipitation, or absorption either alone or in combination.

In addition to crude oil, this process is also applicable to hydrocarbon phases such as condensates, naphthas, middle distillates, and waxes.

In more detail, the disclosure comprises one or more embodiments, described as follows:

One embodiment is a method of removing mercury from crude oil, comprising heating crude oil comprising mercury in various forms to at least 100° C. and less than 350° C. until at least 95% of the mercury in various forms is converted to elemental mercury; converting the elemental mercury to gaseous elemental mercury; and removing the gaseous elemental mercury.

Preferably, the heating occurs for a time sufficient to convert at least 95% all mercury forms to elemental mercury. Preferably 96, 97, 98, 99 or nearly 100% of the mercury is converted. Preferred temperature ranges from 150-300° C., but can be higher if chemical changes to the crude are also desired.

Preferably, the converting step is by flashing or gas stripping, but any other method can be used.

The removing step can be by any known in the art or to be developed in the future, and includes condensation, precipitation, or absorption, adsorption, and combinations thereof.

Preferred removal methods include removing mercury from said mercury rich gas stream by precipitation as HgS. Another method includes treating said mercury rich gas stream with an adsorption agent. Yet another method includes removing mercury from said mercury rich gas stream by precipitation as HgSe after contacting said mercury rich gas stream with a filter containing selenium.

Another embodiment is an improved method of removing mercury from crude oil, the method comprising contacting a liquid hydrocarbon stream having mercury contaminants with a gas stream to thereby form a treated liquid stream and a mercury rich gas stream, wherein the improvement comprises first heating liquid hydrocarbon stream having mercury contaminants at 100-350° C. until most of the mercury contaminants are converted to elemental mercury.

Yet another embodiment is an improved method of removing mercury from crude oil, the method comprising determining the exact mercury speciation in a crude oil sample; calculating the reaction rate expressions for the crude oil sample using the previously determined mercury speciation; heating the crude oil comprising mercury in various forms to at least 100° C. and less than 350° C. until at least 95% of the mercury in various forms is converted to elemental mercury, wherein the reaction rate expression will be used to determine how long the crude oil should be heated; converting the elemental mercury to gaseous elemental mercury; and removing the gaseous elemental mercury.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention, such as instructions for use, buffers, vessels, and the like.

The following abbreviations are used herein:

| ABBREVIATION | TERM |
| --- | --- |
| ID-ICP-MS | isotope dilution inductively coupled plasma mass spectrometry |
| gpm/ft$^2$ | gallons per minute per square foot of cross sectional surface area |
| GC | Gas chromatography |
| Hg$^0$ | Elemental mercury |

DETAILED DESCRIPTION

Figure 1:
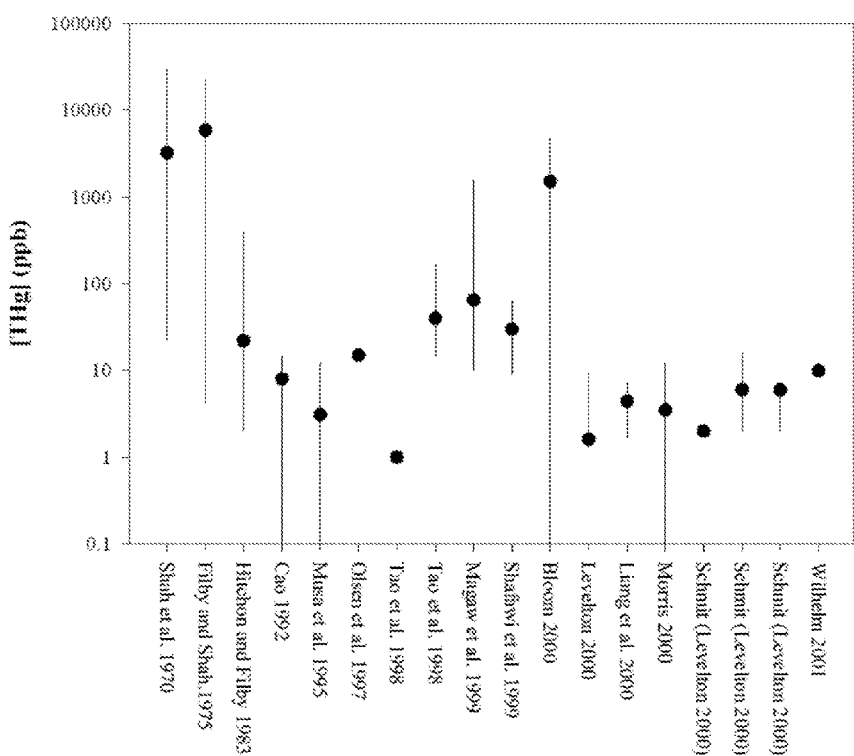
FIG. 1. Literature values of concentrations of mercury in crude oil, from Hollebone 2007.

The following description is intended to be illustrative only, and not unduly limit the scope of the appended claims. The present invention is exemplified with respect to crude oils. However, this is exemplary only, and the invention can be broadly applied to a variety of hydrocarbons.

Mercury can exist in many different forms in crude oil and these compounds can vary widely in their toxicity, reactivity, volatility, and solubility. It is therefore essential to know which forms of mercury are present in order to design systems for mercury removal and pollution control and to assess the impact of mercury on important issues such as occupational exposure, mechanical integrity, and refinery/petrochemical processes.

A key conclusion from our preliminary work in this regard was that our knowledge of mercury speciation in oils and condensates was inadequate. We knew that the root cause for this knowledge gap was that the analytical methodology needed to properly analyze mercury species did not exist.

Speciation and fractionation are two approaches for characterizing the behavior of an element within a given system. Elemental speciation refers to the analytical process of identifying and quantifying the individual chemical forms of an element that are present in a material. If direct detection of the species is not possible, then a sample preparation step such as a chromatographic separation or a chemical derivatization may be required.

Elemental fractionation refers to the analytical process of partitioning an element into a series of fractions based on differences in properties such as solubility, boiling point, particle size, volatility, and reactivity. This approach typically does not provide specific chemical identification.

Speciation provides important information for understanding the fate and distribution of mercury throughout the petroleum system from reservoir rock to consumer products.

Mercury Speciation in Crude Oil

Although speciation techniques are well developed for aqueous media, the technology for speciating mercury in crude oil is not as mature. The speciation and fractionation of mercury in crude oil is a particularly difficult task because of the low concentrations involved and because of the complexity of mercury chemistry.

This complexity is due in part to the fact that many of the mercury species can exist in multiple phases (gas, liquid, solid) simultaneously. For example, elemental mercury can be found in the headspace gas, dissolved in the crude oil, adsorbed to particulate matter, and as discrete droplets suspended in the oil.

The total concentration of mercury will be equal to the sum of the contributions from each of the various forms of mercury as shown below:

$$Hg_{total} = Hg^0 + Hg^{2+}_{complex} + Hg_{ads} + Hg_{other}$$

where:

$Hg_{total}$=the sum total of all the species of mercury $Hg^0$=elemental mercury (can exist in gaseous, liquid, or solid phases)

$Hg^{2+}_{complex}$=organically-complexed ionic mercury (mercury-thiols, etc.)

$Hg_{ads}$=mercury adsorbed to solid particles or metallic surfaces $Hg_{other}$=other forms of mercury not listed above Each of these species is characterized by a unique set of properties that define its toxicity, solubility, volatility, thermal stability, and reactivity. Further, is very likely that mercury speciation will change as the sample ages and this must be taken into account when interpreting the results of the analytical measurements.

In order to study the kinetics of mercury transformation reactions in crude oils, an accurate procedure is needed for determining the species of mercury that are present. The art is lacking an accurate mercury speciation procedure applicable to crude oil matrices did not exist. We developed a mercury speciation procedure, described herein, to fill this technology gap. The forms of mercury that can be determined using our procedure are $Hg^0$ (elemental mercury), $Hg(CH_3)_2$ (dimethyl mercury), $HgCH_3X$ (monomethyl mercury), and $Hg^{2+}$ (ionic mercury).

Briefly, to determine the mercury species present, samples of the crude oil being processed are spiked with isotopic mercury standards (e.g. $Hg^0$ and $Hg^{2+}$) before undergoing a derivatization process that will derivatize many forms of mercury and separating the derivatized mercury species based on their boiling points using a gas chromatograph (GC). As each mercury species exits the GC, its concentration is determined using an isotope dilution inductively coupled plasma mass spectrometer (ID-ICP-MS). This method is described using $^{199}Hg^0$ and $^{198}HgCl_2$ as the isotopic standards. However, other isotopic mercury standards such as HgO can be used.

This chemical derivatization method, described in more detail below, prevents thermal conversion of $Hg^{2+}$ during the GC separation of the species by converting $Hg^{2+}$ to diethyl mercury and converting monomethyl mercury into methylethyl mercury. $Hg^0$ and dimethyl mercury are not altered by the derivatization.

Preparation of Isotopically Enriched $Hg^0$ Standard:

20 mg of mercuric oxide (Oakridge National Laboratory, USA) enriched in the 199 or 200 isotope is dissolved in 2 ml of concentrated hydrochloric acid (HCl) then diluted with water to a final HCl concentration of 20%. Approximately 0.5 g of stannous chloride [$SnCl_2$] is added to the solution, then stirred 4 hours until droplets of metallic Hg form. These $Hg^0$ droplets are washed three times with concentrated HCl. The acid washing is followed by water, methanol, and toluene washes. The $Hg^0$ droplets can be stored at room temperature in a borosilicate glass test tube in approximately 10 ml of ultrapure heptane to yield a saturated solution with approximately 800 ng/g of $^{199}Hg^0$ or $^{200}Hg^0$.

Preparation of Isotopically Enriched $Hg^{2+}$ Standard:

1 mg of mercuric oxide (Oakridge National Laboratory, USA) enriched in the 198 or 201 isotope is dissolved in 1 ml of concentrated HCl. The solution is evaporated under a gentle stream of nitrogen at 90° C. to produce a dry mercuric chloride powder. The mercuric chloride powder is dissolved in 10 g of ultrapure toluene. This solution can be stored at −20° C. in a borosilicate glass test tube. The final concentration of the $^{198}Hg^{2+}$ or $^{201}Hg^{2+}$ in these standards can be determined by reverse isotope dilution, using a toluene solution of natural isotopic abundance $HgCl_2$ ($HgCl_2$ 99.999%, Sigma Aldrich).

Preparation of Crude Oil Samples:

Crude oil samples are prepared for speciation analysis by accurately weighing approximately 0.1 g of crude oil into a 2 ml borosilicate glass GC vial. These vials are sealed using commercially available GC crimp caps and red rubber/PTFE septa. Approximately 5-8 mg each of the $^{199}Hg^0$ and $^{198}HgCl_2$ standard solutions are added to the samples via injection through the septa using 10 μl gas-tight syringes. Dedicated syringes are used for each of the isotope standard solutions to prevent cross-contamination.

The added masses of the isotope standards are measured gravimetrically using a 5-decimal place analytical balance. The isotopic mercury standards are mixed with the crude oil solution by manually swirling the GC vials in a circular motion. The solution is allowed to equilibrate for 30 minutes before derivatization.

Derivatization:

The crude oil samples with the isotope standards (isotopically spiked samples) are derivatized using a procedure we have optimized to minimize unwanted Hg species redistribution reactions. Here, 10 μl of 2M ethylmagnesium chloride (EtMgCl) in THF is injected through the GC vial septum using a gas-tight syringe, followed by 0.5-1 ml of ultrapure heptane using a 2 ml disposable syringe fitted with a 20 mm 27 gauge needle. The heptane lowers the solution viscosity to facilitate the derivatization reaction between the EtMgCl and mercury components in the crude oil. The samples are then derivatized at 0° C. for 20 minutes before GC/ICP-MS analysis.

By using this mercury speciation method, we have determined that crude oils contain two basic forms of mercury: elemental mercury ($Hg^0$) and ionic mercury ($Hg^{2+}$). Ionic mercury is very soluble in crude oils and is a non-volatile form of mercury. Elemental mercury, in contrast, is less soluble and more volatile. This has important implications for the design of processes to remove mercury from crude oil because it affects the reaction rate expression. Based on this knowledge of mercury speciation in crude oil, we have developed a process for removing mercury from crude oils.

Converting Mercury Forms to Elemental Mercury

In crude oil, the elemental mercury redox equilibrium, $Hg^0 \leftrightarrow Hg^{2+} + 2e^-$, is shifted towards the oxidized state ($Hg^{2+} + 2e^-$) at temperatures below 100° C. The equilibrium begins to shift towards the reduced state at temperatures above 100° C. Although the $Hg^{2+}$ reduction rate is too small at 100° C. to be commercially useful, the conversion to $Hg^0$ will be complete in a petroleum reservoir at that temperature because of the geologic timescale that applies to that environment (>10 million years). As such, the mercury concentration and speciation in wellhead crude oil is a function of reservoir geology and temperature.

Additionally, mercury speciation undergoes predictable changes as the physical and chemical conditions change during oil production and transport. In crude oil reservoirs at temperatures above 100° C., mercury is present only as $Hg^0$. After the crude is extracted from the reservoir and its temperature falls below 100° C., the spontaneous oxidation of $Hg^0$ to $Hg^{2+}$ will occur.

$Hg^{2+}$ is very soluble in crude oils and is a non-volatile form of mercury, making its removal more difficult. Thus, preheating oils to at least 100° C. will convert $Hg^{2+}$ to $Hg^0$, and simplify extraction because processes to remove elemental mercury already exist.

For example, U.S. Pat. No. 4,962,276 and U.S. Pat. No. 8,080,156 disclose processes that employ gas stripping to remove mercury from condensates and crude oils. These processes, however, only work if the mercury is in the gas strippable elemental form. As noted above, a significant portion of the mercury in a crude oil can be present in the non-volatile ionic form. The non-volatile ionic mercury cannot be removed from a crude oil by gas stripping. Each of these methods can be used however, if proceeded by the preheat stage described herein, which converts various forms of mercury to elemental mercury.

U.S. Pat. No. 5,384,040 discloses a catalytic process for transforming mercury compounds contained in a gas condensate liquid into elemental mercury. Although not the preferred embodiment, a non-catalytic heat treatment process in the absence of hydrogen is also disclosed. The elemental mercury formed by the catalytic process is removed from the gas condensate liquid using a solid phase sorbent.

In this disclosure, a process is described for converting the various forms of mercury in a crude oil to the elemental form so that the mercury can be subsequently removed from the oil by gas stripping.

Figure 2:
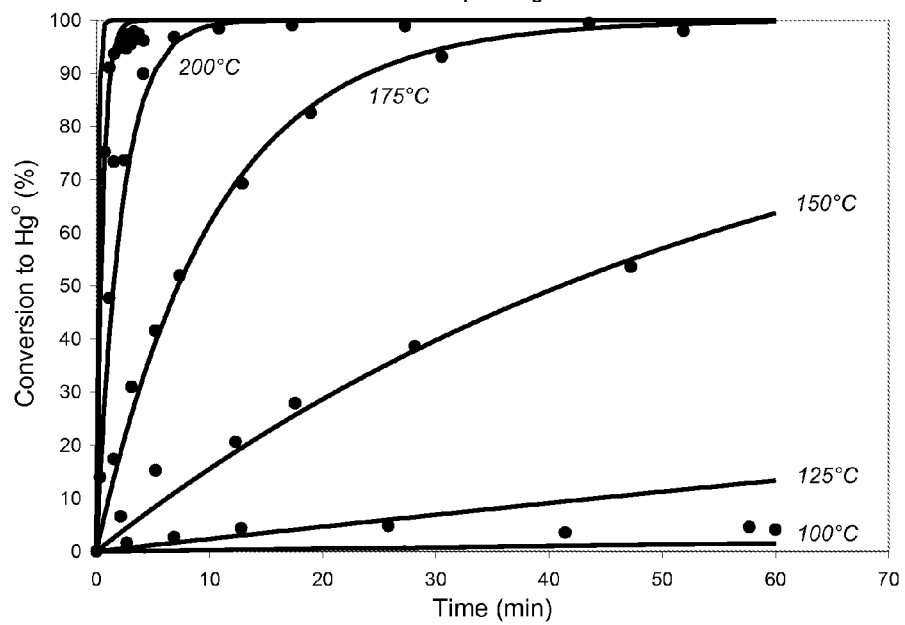
FIG. 2. Reduction of mercuric ion to elemental mercury with time at seven different temperatures (100-250° C., in 25° C. increments) in a crude oil matrix.

In such process, crude oil is heated to a temperature above 100° C. and held at that temperature for a specified period of time to convert all of the forms of mercury in the oil into the elemental mercury form. As shown in FIG. 2, the rate of conversion to elemental mercury increases with temperature, and the temperature should not be lower than 100° C.

The amount of mercury removed from the oil can be controlled by adjusting the temperature and/or the length of time that the oil is held at a specified temperature per FIG. 2. However, the temperature preferably does not exceed the decomposition temperature of the hydrocarbon.

The rate at which mercury is thermally reduced to elemental mercury is also strongly influenced by the composition of the crude oil. Therefore, for process design purposes, it is important to experimentally determine the kinetics of the mercury reduction reaction for the specific oil feed to the process.

Kinetic data for the mercury reduction reaction are obtained by spiking the oil with an enriched stable isotope of ionic mercury (e.g. $198Hg^{2+}$ or $^{201}Hg^{2+}$). To accomplish this, an enriched isotope, in the form of $HgCl_2$ or $HgO$ for example, is dissolved in the oil and the rate of conversion of this ionic mercury standard to elemental mercury is monitored as a function of time and temperature. The use of an enriched isotope allows the reduction reaction to be monitored accurately even though naturally-occurring mercury may also be present in the oil.

Rapid, time-resolved sampling is essential for building the accurate kinetic models that are needed for designing mercury removal processes. The kinetic data shown in FIG. 2 was produced using a stirred high-pressure batch reactor that allows rapid sampling of the crude oil during a reduction experiment.

The conversion of $Hg^{2+}$ to $Hg^0$ was monitored using enriched isotopic tracers and the mercury speciation procedure that was described above.

The results of the kinetic measurements can be used to define a reaction rate expression for a specific oil that might have a form such as:

$$[Hg^{2+}]_t = [Hg^{2+}]_i e^{-kt}$$

$$k = Ae^{-Ea/RT}$$

where: k=apparent first-order rate constant; t=time; $[Hg^{2+}]_i$=concentration of ionic mercury at time zero; $[Hg^{2+}]_t$=concentration of ionic mercury at time t; $Ae^{-Ea/RT}$ is the Arrhenius equation used to calculate the effect of temperature (T) on the reaction rate constant.

The solid lines in FIG. 2 represent the kinetic behavior predicted using the Arrhenius parameters of the above equations for the specific crude oil that was used in the experiments.

The kinetics, fluid flow and heat transfer of a process are most important when upscaling for large-scale designs. To retain the same reaction rate, the other variables in the process design must be decreased or increased as necessary. For instance, increasing vessel sizes could decrease the rate, such that the temperature of the conversion must be increased to return the rate to its original value. Alternatively, increasing temperature increases the amount and rate of mercury conversion, See FIG. 2. However, a balance must be struck to prevent thermal degradation of other components in the crude oil or destruction of processing equipment. Thus, the above reaction rate expression and the Arrhenius equation are used to calculate process design specifications such as process temperature, vessel sizes, oil feed rate, oil recycle rate, etc.

The process temperature for the ionic mercury reduction step should be in the range of 100-350° C. More preferably the process temperature should be in the range of 100-300° C. Most preferably the process temperature should be in the range of 150-300° C. This temperature range is compatible with standard crude oil processing equipment, such as the stabilization units that are used in NGL extraction. The optimum process temperature will vary based on the composition of the oil and the desired reaction rate.

Following the ionic mercury reduction step, the crude oil is flashed and/or stripped with gas to transfer the elemental mercury from the oil phase into the gas phase.

Elemental mercury can then be removed from the mercury enriched gas phase by methods such as condensation, precipitation, amalgamation, adsorption, or absorption alone or in combination. If desired, some or all of the stripping gas can be recycled back into the process.

Figure 3:
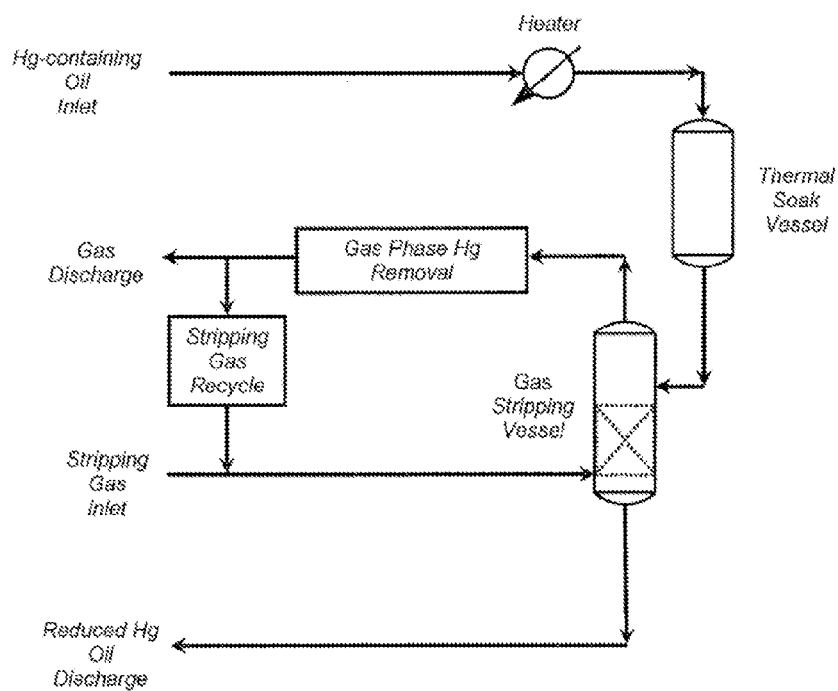
FIG. 3. Schematic of a process for removal of mercury from crude oil.

A block flow diagram of the disclosed process is shown in FIG. 3. The crude oil is introduced into a heater to quickly and efficiently preheat the crude oil to at least 100° C. The heated oil is then moved into a thermal soak vessel that is heated to a pre-determined temperature above 100° C. The crude remains in the heated soak vessel while the mercury species are being converted into elemental mercury. After conversion, the crude oil flows into a gas stripping vessel with an optional packing therein to facilitate contact between a stripping gas and crude oil. As shown in FIG. 3, the stripping gas flows from the bottom of the vessel through the oil. Any gas, such as nitrogen, methane, ethane, propane, butane, or natural gas, can be used.

As the stripping gas contacts the crude oil, the elemental mercury is removed in the form of mercury gas. The stripping gas plus mercury vapor is drawn from the top of the vessel and passed through a mercury removal unit, wherein the mercury can be removed from the stripping gas using an adsorption method (filter or scrubber). Alternative, mercury can be removed from the stripping gas via precipitation with a filter containing selenium or a gas containing hydrogen sulfide.

The mercury-free stripping gas can then be recycled. The stripped crude oil will be discharged for further processing.

Any gas stripping technique known in the art, such as those described below, can be used to separate the elemental mercury from the liquid/solid crude as long as the operation temperatures are at least 200° C.

U.S. Pat. No. 4,962,276 describes a method for removing mercury from hydrocarbon condensate comprising:
  providing a stripper having a top, a bottom, and a packing therein;
  forming said hydrocarbon condensate into a spray;
  introducing said spray into said stripper and into contact with said packing;
  flowing a gas stream through said stripper, thereby stripping mercury from said hydrocarbon condensate;
  removing said stripped hydrocarbon condensate from the bottom of said stripper; and
  removing said gas, including said stripped mercury, from the top of said stripper.

In the U.S. Pat. No. 4,962,276 patent, mercury-contaminated liquid is introduced near the top of a stripper in the form of a spray or mist. A stripping gas is introduced near the bottom of the stripper. The stripper includes a first outlet at or near the bottom thereof and a second outlet at or near the top. A packing made from structural packing material or the like is provided to increase the exposure of the liquid to the stripping gas.

The stripping gas flows through the stripper and removes mercury as mercury vapor from the condensate or water. Cleaned product is drawn from the bottom outlet, while the mercury-containing gas exits through the top outlet. The residence time of the water or condensate within the stripper is up to about thirty minutes, with one to ten minutes being the preferred range. The liquid flux rate is 1-200 gpm/ft$^2$ or 5-50 gpm/ft$^2$. Gas flux rate is between 50-5,000 ft$^3$/m/ft$^2$ or 300-1,000 ft$^3$/m/ft$^2$. If condensate is treated, the pressure within the stripper is between about 0-1,000 psi, and preferably 0-500 psi.

The stripping operation is conducted at a temperature of at least 200° F. Higher temperature ranges may be preferred, such as 300-500° F., if light hydrocarbons are also removed. Upon mercury removal, the vapor can be condensed to recover the light hydrocarbons. Less stripping gas is required at higher operating temperatures.

The stripping gas utilized in the process may be any of a number of gases including, for example, air, $N_2$, $CO_2$, $H_2$, or natural gas. Natural gas is preferred for the removal of mercury from hydrocarbon condensate because of its availability and due to the fact that it may be recovered as the product subsequent to purification.

A mercury adsorber or a scrubber is used to treat the stripping gas after it exits the stripper. The adsorber may include a fixed bed of active solid adsorbents such as sulfur/carbon, Ag/carbon, Ag/$Al_2O_3$, CuS/$Al_2O_3$, CuS/carbon, FeS/$Al_2O_3$, FeS/carbon or Bi/$Al_2O_3$, and the like. The adsorber should be sufficiently large to remove ninety percent of the mercury from the stripping gas. Typical superficial gas velocity through the bed should be between 0.1-50 ft/s and preferably one half to ten feet per second. Depending upon the nature and activity of the adsorbent, the temperature should be maintained at 50-400° F.

A polysulfide scrubbing system may alternatively be used to remove mercury from the stripping gas. The mercury-containing stripping gas is passed through a scrubbing tower where it is scrubbed with a dilute alkali solution of $Na_2S_x$. The tower is preferably packed with structural packing, although a bubble cap or sieve tray could also be employed.

Other known processes may be used to adsorb mercury vapor from the stripping gas. U.S. Pat. No. 3,194,629 discloses one such process.

U.S. Pat. No. 8,080,156 describes a preferred process for removing elemental mercury by transferring elemental mercury from a liquid hydrocarbon stream to a natural gas stream. The transferring occurs by contacting the liquid hydrocarbon stream with the natural gas stream to thereby form a treated liquid stream and a mercury rich gas stream. In addition, the method includes removing mercury from the mercury rich gas stream.

For one embodiment in U.S. Pat. No. 8,080,156, a process includes separating a crude oil stream into a gaseous hydrocarbon stream and a liquid hydrocarbon stream, removing mercury from the gaseous hydrocarbon stream to provide a treated gas stream, and introducing the treated gas stream into contact with the liquid hydrocarbon stream to transfer mercury from the liquid hydrocarbon stream to the treated gas stream and thereby form a treated liquid stream and a mercury rich gas stream. Separating the treated gas stream to remove propane and butane from the treated gas stream occurs prior to contacting the treated gas stream with the liquid hydrocarbon stream. Introducing a pentane-plus vapor stream separated from the treated gas stream into contact with the treated liquid stream enables absorbing the pentane-plus vapor stream into the treated liquid stream. Removing mercury from the mercury rich gas stream provides recycled gas that provides part of the treated gas stream.

Figure 4:
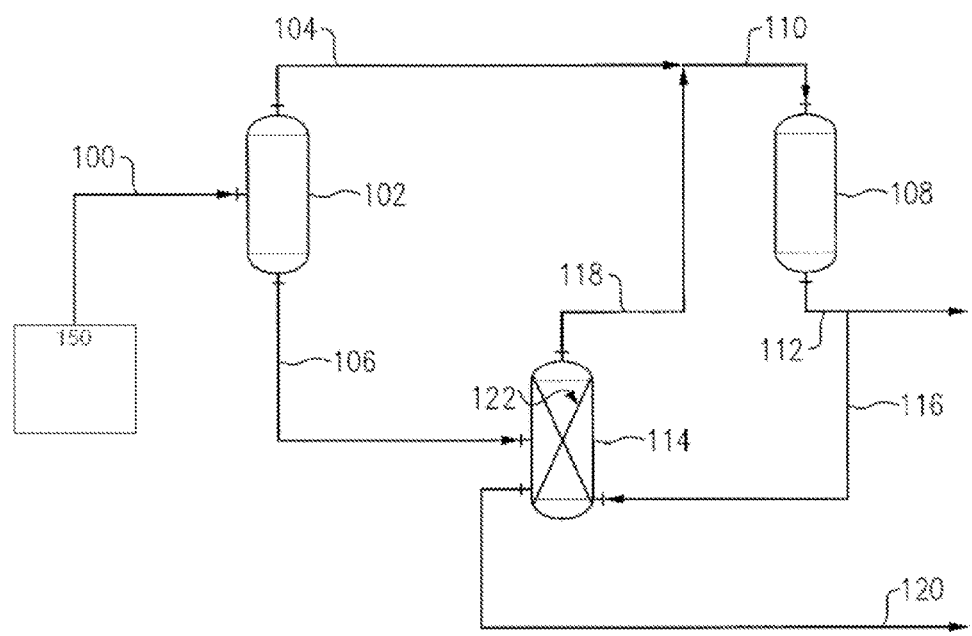
FIG. 4. Simplified schematic flow diagram of an assembly for removing mercury from preheated crude oil, according to one embodiment.

FIG. 4 (adapted from U.S. Pat. No. 8,080,156) illustrates a system in which 100-350° C. preheated crude oil (150) is sent by line 100 and is passed to a separator 102 for separation into a gaseous hydrocarbon stream comprising, consisting of, or consisting essentially of hydrocarbons, elemental mercury and water, which is removed from the separator 102 by line 104, and into a liquid hydrocarbon stream: 1) comprising, consisting of, or consisting essentially of hydrocarbons and elemental mercury, or 2) comprising, consisting of, or consisting essentially of hydrocarbons, elemental mercury and water, which is removed from the separator 102 by line 106. A mercury-containing gas feed, including in part at least a portion of the gaseous hydrocarbon stream, is charged to a mercury removal unit (MRU) 108 by line 110 for removal of mercury from the mercury-containing gas feed, thereby forming a treated gas stream, which is removed from the MRU 108 by line 112. A recycle gas stream comprising a portion of the treated gas stream from the line 112 is charged to a contactor 114 by line 116 for contact with at least a portion of the liquid hydrocarbon stream charged to the contactor 114 by the line 106. Through such contacting, at least a portion of the elemental mercury contained in the liquid hydrocarbon stream is transferred to the recycle gas stream, thereby forming a mercury rich gas stream, which is removed from the contactor 114 by line 118, and a treated liquid hydrocarbon stream, which is removed from the contactor 114 by line 120. The mercury rich gas stream is passed to the MRU 108 as a portion of the mercury-containing gas feed by the lines 118 and 110.

For some embodiments, the contactor 114 includes multiple (e.g., 2, 4, 6 or more) theoretical stages 122 (depicted by "X" within the contactor 114) of separation between vapor and liquid phases. Either trays or packing material in a flow path of fluids described herein passing through the contactor 114 may form the theoretical stages 122. For example, the packing material disposed inside of the contactor 114 to define the stages 122 may include random oriented objects or a shaped structure and may be made of metallic or ceramic solid material. In some embodiments, amount of the packing material utilized depends on a desired number of the stages 122 provided by the packing material.

Figure 5:
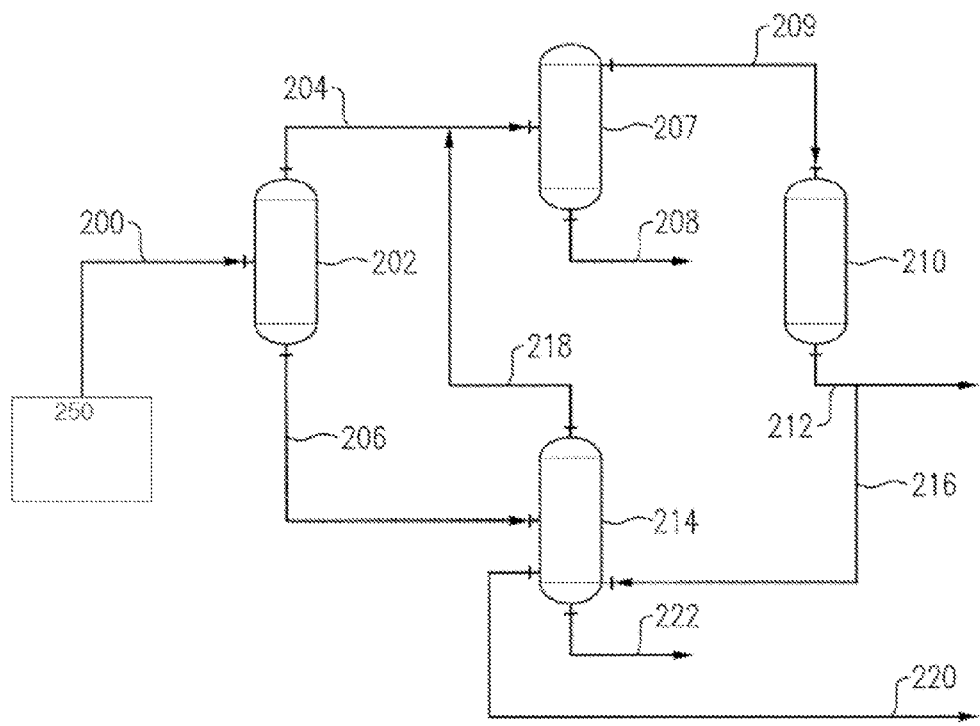
FIG. 5. Simplified schematic flow diagram of another assembly for removing mercury from preheated crude oil, according to another embodiment.

FIG. 5 (adapted from U.S. Pat. No. 8,080,156) shows a system in which preheated crude oil 250 is passed by line 200 to a first separator 202 for separation into a gaseous hydrocarbon stream comprising, consisting of, or consisting essentially of hydrocarbons, mercury and water, which is removed from the first separator 202 by line 204, and into a liquid hydrocarbon stream comprising, consisting of, or consisting essentially of hydrocarbons, elemental mercury and water, which is removed from the separator 202 by line 206. Along with a mercury rich gas stream described later, the gaseous hydrocarbon stream is charged to a second separator 207 wherein water is removed and exits the second separator 207 by line 208. Overhead gases leaving the second separator 207 by line 209 are charged to a mercury removal unit (MRU) 210 as a mercury-containing gas feed for removal of mercury from the mercury-containing gas feed, thereby forming a treated gas stream, which is removed from the MRU 210 by line 212. A recycle gas stream comprising a portion of the treated gas stream from line 212 is charged to a contactor 214 by line 216 for contact with at least a portion of the liquid hydrocarbon stream charged to the contactor 214 by the line 206. Through such contacting, at least a portion of the elemental mercury contained in the liquid hydrocarbon stream is transferred to the recycle gas stream, thereby forming a mercury rich gas stream, which is removed from the contactor 214 by line 218, and a treated liquid hydrocarbon stream, which is removed from the contactor 214 by line 220. The mercury rich gas stream is passed to the second separator 207 along with the gaseous hydrocarbon stream by the lines 218 and 204. In addition, water is separated from the liquid hydrocarbon stream (and from the recycle gas stream, if water is present in such) and removed from the contactor 214 by line 222. For some embodiments, a third separator is included in between the first separator 202 and the contactor 214 to separate water from the liquid hydrocarbon stream 206. In some embodiments, a heat exchanger is included after the first separator 202 to increase temperature of the liquid hydrocarbon stream and achieve adequate separation of water from the liquid hydrocarbon stream 206.

The following references are incorporated by reference in their entirety.

Salvá et al (2010) SPE 138333.
Hollebone, B. P. and C. X. Yang, "Mercury in Crude Oil Refined in Canada", Environment Canada, Ottawa, ON, 2007.
U.S. Pat. No. 3,194,629
U.S. Pat. No. 4,962,276
U.S. Pat. No. 5,384,040
U.S. Pat. No. 6,350,372
U.S. Pat. No. 6,537,443
U.S. Pat. No. 6,685,824
U.S. Pat. No. 6,806,398
U.S. Pat. No. 8,080,156

The invention claimed is:

1. A method of removing mercury from crude oil, consisting of:
    a) heating crude oil comprising mercury in various forms to at least 100° C. and less than 350° C. until at least 95 wt % of the mercury in various forms is converted to elemental mercury;
    b) converting the elemental mercury to gaseous elemental mercury; and
    c) removing the gaseous elemental mercury.

2. The method of claim 1, wherein said heating is at 100° C.-300° C.

3. The method of claim 1, wherein said heating is at 150° C.-300° C.

4. The method of claim 1, where said converting step is by gas stripping.

5. The method of claim 1, where said removing step is by condensation, precipitation, absorption, adsorption, or combinations thereof.

6. A method of removing mercury from crude oil, consisting of:
    a) heating crude oil comprising mercury in various forms to at least 100° C. and less than 350° C. until at least 95 wt % of the mercury in various forms is converted to elemental mercury;
    b) converting the elemental mercury to gaseous elemental mercury by flashing; and
    c) removing the gaseous elemental mercury.

7. An improved method of removing mercury from crude oil, the method comprising contacting a liquid hydrocarbon stream having mercury contaminants with a gas stream to thereby form a treated liquid stream and a mercury rich gas stream, wherein the improvement comprises first heating liquid hydrocarbon stream having mercury contaminants at 100-350° C. until 95 wt % of said mercury contaminants are converted to elemental mercury.

8. The improved method of claim 7, wherein said gas stream is nitrogen, methane, ethane, propane, butane, or natural gas.

9. The improved method of claim 7, wherein said gas stream is a natural gas stream.

10. The improved method of claim 7, further comprising removing mercury from said mercury rich gas stream.

11. The improved method of claim 7, further comprising removing mercury from said mercury rich gas stream by precipitation as HgS, wherein said gas stream contains hydrogen sulfide.

12. The improved method of claim 11, further comprising treating said mercury rich gas stream with an adsorption agent.

13. The improved method of claim 7, further comprising removing mercury from said mercury rich gas stream by precipitation as HgO.

14. The improved method of claim 7, further comprising removing mercury from said mercury rich gas stream by precipitate as HgSe after contacting said mercury rich gas stream with a filter containing selenium.

15. A method of removing mercury from crude oil, comprising:
    a) determining the mercury speciation in said crude oil;
    b) calculating a reaction rate expression, wherein said reaction rate expresses the conversion of ionic mercury into elemental mercury;
    c) heating crude oil comprising mercury in various forms to at least 100° C. and less than 350° C. until at least 95 wt % of the mercury in various forms is converted to elemental mercury, wherein said 95% conversion is calculated using said reaction rate expression;
d) converting the elemental mercury to gaseous elemental mercury; and
e) removing the gaseous elemental mercury.

16. The method of claim 15, wherein determining said mercury speciation comprises spiking a crude oil sample with enriched isotopic mercury standards; derivatizing said spiked crude oil sample with 10 μl of 2M ethylmagnesium chloride (EtMgCl) in THF and 0.5-1 ml of ultrapure heptane at 0° C. for 20 minutes; and analyzing derivatized mercury species in said spiked crude oil using GC/ICP-MS.

17. A method of determining mercury speciation in crude oil, comprising:
a) adding isotopic mercury standards to a crude oil sample;
b) derivatizing all forms of mercury in said crude oil sample, wherein 10 μl of 2M ethylmagnesium chloride (EtMgCl) in THF and 0.5-1 ml of ultrapure heptane are added to crude oil sample and allowed to react at 0° C. for 20 minutes;
c) separating derivatized mercury forms based on boiling points in a GC; and
d) determining concentration of derivatized mercury forms based on relative concentration to isotopic mercury standards using ICP-MS.

18. The method of claim 17, wherein the forms of mercury include $Hg^0$ (elemental mercury), $Hg(CH_3)_2$ (dimethyl mercury), $HgCH_3X$ (monomethyl mercury), and $Hg^{2+}$ (ionic mercury).

* * * * *